United States Patent
Sato

(10) Patent No.: US 8,269,400 B2
(45) Date of Patent: Sep. 18, 2012

(54) ULTRASONIC TRANSDUCER, ULTRASONIC DIAGNOSIS APPARATUS USING THE SAME, AND ULTRASONIC FLAW INSPECTION APPARATUS USING THE SAME

(75) Inventor: Toshiharu Sato, Tokyo (JP)

(73) Assignee: Panasonic Corporation, Osaka (JP)

( * ) Notice: Subject to any disclaimer, the term of this patent is extended or adjusted under 35 U.S.C. 154(b) by 304 days.

(21) Appl. No.: 12/667,903

(22) PCT Filed: Jun. 20, 2008

(86) PCT No.: PCT/JP2008/001595
§ 371 (c)(1),
(2), (4) Date: Jan. 6, 2010

(87) PCT Pub. No.: WO2009/011089
PCT Pub. Date: Jan. 22, 2009

(65) Prior Publication Data
US 2010/0191108 A1    Jul. 29, 2010

(30) Foreign Application Priority Data
Jul. 19, 2007    (JP) ................. 2007-187917

(51) Int. Cl.
*H01L 41/08* (2006.01)
(52) U.S. Cl. .................................................. 310/334
(58) Field of Classification Search ........... 310/334–337
See application file for complete search history.

(56) References Cited

U.S. PATENT DOCUMENTS

| | | | | |
|---|---|---|---|---|
| 4,277,712 A | * | 7/1981 | Hanafy | 310/334 |
| 5,381,385 A | * | 1/1995 | Greenstein | 367/140 |
| 5,938,612 A | * | 8/1999 | Kline-Schoder et al. | 600/459 |
| 6,121,718 A | * | 9/2000 | Mohr, III | 310/334 |
| 6,761,688 B1 | * | 7/2004 | Mohr et al. | 600/437 |
| 7,156,938 B2 | * | 1/2007 | Baumgartner et al. | 156/150 |
| 7,679,270 B2 | * | 3/2010 | Nakamura | 310/334 |
| 7,795,786 B2 | * | 9/2010 | Nakayama et al. | 310/334 |
| 2002/0073781 A1 | | 6/2002 | Hashimoto et al. | |

(Continued)

FOREIGN PATENT DOCUMENTS

DE    10-2004-054-293 A1    6/2005
(Continued)

OTHER PUBLICATIONS

Foreign Office action for 7102 024 WO/DE dated Feb. 15, 2011.
(Continued)

*Primary Examiner* — Mark Budd
(74) *Attorney, Agent, or Firm* — Pearne & Gordon LLP

(57) ABSTRACT

A technique that provides: an ultrasonic transducer in which the accurate arrangement of piezoelectric elements and the electric conductive state between electrode layers are reserved; and an ultrasonic diagnosis apparatus and an ultrasonic flaw inspection apparatus which use the ultrasonic transducer is provided. According to the technique, a plurality of piezoelectric elements 1, each being a stacked body in which predetermined numbers of piezoelectric layers 2 and electrode layers 3 are alternately stacked and although this has both sides that are substantially flat along a stacking direction, side electrodes 6 to connect the predetermined electrode layers 3 are placed outside both of the sides, are arranged in a direction orthogonal to the stacking direction, wherein an interval holding member 10 having a predetermined thickness is put between the sides on which the side electrodes 6 of the piezoelectric elements 1 adjacent to each other are formed.

13 Claims, 6 Drawing Sheets

U.S. PATENT DOCUMENTS

2005/0099096 A1     5/2005     Baumgartner et al.

FOREIGN PATENT DOCUMENTS

| | | |
|---|---|---|
| JP | 01-174199 A | 7/1989 |
| JP | 11-299779 A | 11/1999 |
| JP | 2001-309493 A | 11/2001 |
| JP | 2001-309497 A | 11/2001 |
| JP | 2002-186617 A | 7/2002 |
| JP | 2005-210245 A | 8/2005 |

OTHER PUBLICATIONS

International Search Report for PCT/JP2008/001595.

\* cited by examiner

ULTRASONIC TRANSDUCER, ULTRASONIC DIAGNOSIS APPARATUS USING THE SAME, AND ULTRASONIC FLAW INSPECTION APPARATUS USING THE SAME

TECHNICAL FIELD

The present invention relates to an ultrasonic transducer that is used in a medical field, such as a diagnosis, a treatment and the like, and an industrial field such as a non-destructive inspection and the like, and an ultrasonic diagnosis apparatus using the same, and an ultrasonic flaw inspection apparatus using the same.

BACKGROUND ART

An array type ultrasonic transducer in which a plurality of elongated reed-shaped piezoelectric elements are one-dimensionally arranged is widely used in an ultrasonic diagnosis apparatus and the like. In order to attain the higher sensibility of the ultrasonic transducer, a configuration in which a stacked piezoelectric ceramics is used in the reed-shaped piezoelectric element is conventionally used. In a case of using the stacked piezoelectric ceramics, when the number of stacking is n, as compared with a case in which the same frequency is attained in a single layer, under an assumption that a driving voltage is constant, an electric field becomes n times. Thus, a transmitted sound pressure is improved to n times.

FIG. 12A and FIG. 12B show a schematic view of a conventionally-known ultrasonic transducer. FIG. 12A shows the perspective view of the ultrasonic transducer, and FIG. 12B shows its sectional view, respectively. A piezoelectric element 1 is configured as a stacked body in which piezoelectric layers 2 of two layers and electrode layers of three layers are alternately stacked. In the piezoelectric layer 2 of the two layers, their polarization axes are opposite to each other, and in the electrode layer of the three layers, the upper and lower layers serve as ground electrode layers 3b, and the central layer serves as a signal electrode layer 3a, and they are electrically connected to an earth pickup electrode 4 and a signal lead wire 5, respectively.

The ground electrode layer 3b is electrically connected to a side electrode 6 laid onto the side and guided to the lower surface of the piezoelectric element 1 and electrically connected to the earth pickup electrode 4, for example, with soldering, electric conductive adhesive and the like. Similarly, the central signal electrode layer 3a is also guided through the side electrode 6 to the lower surface of the piezoelectric element 1 and connected to the signal lead wire 5. An acoustic matching layer 7 for efficiently transmitting and receiving an ultrasonic wave is formed on the upper portion of the piezoelectric element 1. Also, a rear member 8 for holding the piezoelectric element arrangement and absorbing and attenuating the ultrasonic wave to be emitted to the lower portion of the piezoelectric element 1 is placed in the lower portion of the piezoelectric element 1.

When the one-dimensional array arrangement is formed, a division processing apparatus, for example, such as a dicing saw and the like, is used. Since the division processing apparatus is used to form a division groove that arrives at the rear member 8 from the acoustic matching layer 7, the elongated reed-shaped piezoelectric element 1 is formed in the shape of an array (for example, refer to the following patent document 1).

Since it is divided into the array shapes, the width of the side electrode 6 is made narrower, which results in a possibility that the influence of the processing causes the electric conductive state to be unstable or disconnect. Thus, the sure electric conductive state is required to be reserved. A method of preliminarily forming the reed-shaped piezoelectric element 1 after the division to form the side electrode 6 by using the longitudinal direction side is considered. However, a step of arranging the reed-shaped piezoelectric elements 1 is required. Hence, there is a fear that the arrangement is disturbed.

Also, not only in the one-dimensional arrangement array but also in the two-dimensional arrangement array, the configuration of employing the stacked piezoelectric ceramics is conventionally known. In the two-dimensional arrangement array in which the size of the piezoelectric element 1 is smaller than the one-dimensional arrangement array, the employment of the stacked piezoelectric ceramics provides the effect that the electric impedance of the piezoelectric element 1 is decreased. Thus, this is beneficial.

FIG. 13A and FIG. 13B show schematic views of a conventionally-known two-dimensional arrangement array ultrasonic transducer. FIG. 13A is the schematic view showing the structure of the piezoelectric element, and FIG. 13B shows the schematic view in which a plurality of piezoelectric elements are arranged, respectively. The piezoelectric element 1 is configured as stacking body in which piezoelectric layers 2 of three layers and electrode layers 3 of four layers are alternately stacked. In this case, in the electrode layer 3 of the four layers, the upper first layer and third layer serve as the ground electrode layers 3b, and the second layer and the fourth layer that is the lowest layer serve as the signal electrode layers 3a.

Similarly to the piezoelectric element of the one-dimensional arrangement array, the elongated reed-shaped piezoelectric element 1 (FIG. 13A) is preliminarily formed, and on the two sides whose longitudinal directions are wide, an insulating layer 9 having a predetermined width is formed on the end surface portion of the electrode layer 3 that is not desired to be electrically connected on the side (for example, the signal electrode layer 3a of the second layer, when the ground electrode layers 3b of the upper first layer and third layer are desired to be connected), and the side electrode 6 is formed from thereon, and consequently, the ground electrode layers 3b of the two layers or the signal electrode layers 3a of the two layers are electrically connected.

The plurality of elongated reed-shaped piezoelectric elements 1 on which the side electrodes 6 are formed, respectively, are arranged in line at a predetermined interval in an x-direction as shown in FIG. 13B, and then a gap 10 between the adjacent piezoelectric elements 1 is filled and fixed by using a resin such as adhesive and the like, and then a plurality of division grooves 11 extending in a direction orthogonal to the longitudinal direction of the reed-shaped piezoelectric elements 1, the x-direction in FIG. 13B are formed in a y-direction by using a division processing apparatus, for example, a dicing saw and the like, and they are similarly filled and fixed, thereby forming a two-dimensional piezoelectric element arrangement (for example, refer to the following patent document 2).

Also, in the ultrasonic transducer of a frequency of MHz that is typically used in the ultrasonic diagnosis apparatus and the like, the width of the reed-shaped piezoelectric element 1 is between several 10 μm and several 100 μm, and an interval 10 between the piezoelectric element 1 and the piezoelectric element 1 is several 10 μm, and even the two-dimensional arrangement array has the similar dimensions.

In the case of the conventional two-dimensional arrangement array shown in FIG. 13B, at a step of arranging the elongated reed-shaped piezoelectric elements 1 in line at the predetermined interval 10, it is operationally difficult to arrange the piezoelectric elements 1 each having the width of several 100 μm in line at the gap of several 10 μm. Moreover, it is also difficult to carry out the work for filling the gap 10 with the adhesive and the like in the situation that the element arrangement is kept after the arrangement, and at the time of the working, there is a possibility that the element is slightly moved which results in a positional displacement.

Patent Document 1: Japanese Patent Application Publication H01-174199

Patent Document 1: Japanese Patent Application Publication H11-299779

However, the conventional configuration has a possibility that the disturbance in the element arrangement leads to the disturbance in the generated ultrasonic beam and leads to the drop in a resolution and the quality drop in an ultrasonic diagnostic image. Thus, this has a problem that, when the disturbance in the arrangement is severe, the adjacent elements are brought into contact with each other, which potentially causes the electrical short-circuit and the structural crosstalk.

DISCLOSURE OF THE INVENTION

The present invention is proposed in order to solve the above-mentioned conventional problems and then provides an ultrasonic transducer that can simply attain the reservation of the electric conductive state between electrode layers through a side electrode and an accurate piezoelectric element arrangement, and an ultrasonic diagnosis apparatus and an ultrasonic flaw inspection apparatus that use the ultrasonic transducer.

The ultrasonic transducer according to the present invention has a configuration that a plurality of piezoelectric elements, each being a stacked body in which predetermined numbers of piezoelectric layers and electrode layers are alternately stacked and although this has both sides that are substantially flat along a stacking direction, side electrodes to connect the predetermined electrode layers are placed outside both of the sides, respectively, are arranged in a direction orthogonal to the stacking direction, wherein an interval holding member having a predetermined thickness is put between the sides on which the side electrodes of the piezoelectric elements adjacent to each other are formed.

With this configuration, it is possible to stably reserve the electric conductive state through the side electrode between the electrode layers, and it is possible to have the piezoelectric element in which the piezoelectric property is stable and excellent and the sensibility deterioration is small. Also, the work for accurately arranging the piezoelectric elements at a desirable arrangement interval can be carried out simply. Moreover, the positional dislocation after the arrangement can be protected. Thus, it is possible to provide the ultrasonic transducer in which the crosstalk can be suppressed and the excellent ultrasonic beam can be created.

Also, the ultrasonic transducer according to the present invention has a configuration that the side electrodes of the piezoelectric elements adjacent to each other are placed on the piezoelectric elements so as to be symmetrical with respect to the interval holding member.

With this configuration, the work for accurately arranging the piezoelectric elements at the desirable arrangement interval can be carried out simply. Moreover, the positional dislocation after the arrangement can be protected. Thus, it is possible to provide the ultrasonic transducer in which the crosstalk can be suppressed and the excellent ultrasonic beam can be created.

Also, the ultrasonic transducer according to the present invention is characterized in that at least one of the interval holding members which are respectively put between the piezoelectric elements is made of an electric conductive material.

With this configuration, the electrical connection between the two side electrodes with the interval holding member between can be attained simply and surely without any use of another means. Also, the work for accurately arranging the piezoelectric elements at the desirable arrangement interval can be carried out simply. Moreover, the positional dislocation after the arrangement can be protected. Thus, it is possible to provide the ultrasonic transducer in which the crosstalk can be suppressed and the excellent ultrasonic beam can be created.

Also, the ultrasonic transducer according to the present invention has a configuration that a height of the stacking direction of the interval holding member is lower than a height of the side of the piezoelectric element.

With this configuration, the work for accurately arranging the piezoelectric elements at the desirable arrangement interval can be carried out simply. Moreover, the positional dislocation after the arrangement can be protected. Simultaneously with the fact that the crosstalk can be suppressed and the excellent ultrasonic beam can be formed, the surface contact between the top and bottom surfaces of the piezoelectric element can be made surer, for example, when an acoustic matching layer, a rear member and the like are formed on the top and bottom surfaces of the piezoelectric element. Thus, it is possible to provide the ultrasonic transducer having the excellent property in which the sensibility is high and the frequency band property is wide.

Moreover, the ultrasonic transducer according to the present invention has a configuration that the interval holding member is a double-faced tape.

With this configuration, the work for accurately arranging the piezoelectric elements at the desirable arrangement interval can be carried out simpler. Moreover, the positional dislocation after the arrangement can be protected. Thus, it is possible to provide the ultrasonic transducer in which the crosstalk can be suppressed and the excellent ultrasonic beam can be created.

Also, an ultrasonic transducer according to the present invention has a configuration that a plurality of piezoelectric elements, each being a stacked body in which predetermined numbers of piezoelectric layers and electrode layers are alternately stacked and although this has both sides that are substantially flat along a stacking direction, side electrodes to connect the predetermined electrode layers are placed outside both of the sides, respectively, are arranged in a direction orthogonal to the stacking direction, wherein an interval holding layer is formed on the side electrode of at least one piezoelectric element of the piezoelectric elements adjacent to each other.

With this configuration, it is possible to stably reserve the electric conductive state through the side electrode between the electrode layers, and it is possible to have the piezoelectric element in which the piezoelectric property is stable and excellent and the sensibility deterioration is small. Also, the work for accurately arranging the piezoelectric elements at the desirable arrangement interval can be carried out simply. Moreover, the positional dislocation after the arrangement can be protected. Thus, it is possible to provide the ultrasonic transducer in which the crosstalk can be suppressed and the excellent ultrasonic beam can be created.

Also, an ultrasonic diagnosis apparatus according to the present invention is characterized by including: the ultrasonic transducer according to the present invention as mentioned above; and an ultrasonic diagnosis apparatus body electrically connected to the ultrasonic transducer.

With this configuration, it is possible to use the merit of the ultrasonic transducer according to the present invention and carry out an ultrasonic diagnosis whose precision is high.

Moreover, an ultrasonic flaw inspection apparatus according to the present invention is characterized by including: the ultrasonic transducer according to the present invention as mentioned above; and an ultrasonic flaw inspection apparatus body electrically connected to the ultrasonic transducer.

With this configuration, it is possible to use the merit of the ultrasonic transducer according to the present invention and carry out a non-destructive inspection whose precision is high.

The ultrasonic transducer according to the present invention is designed such that the plurality of piezoelectric elements, each being the stacked body in which the predetermined numbers of the piezoelectric layers and the electrode layers are alternately stacked and although this has both the sides that are substantially flat along the stacking direction, the side electrodes to connect the predetermined electrode layers are placed outside both of the sides, respectively, are arranged in the direction orthogonal to the stacking direction, wherein the interval holding member having the predetermined thickness is put between the sides on which the side electrodes of the piezoelectric elements adjacent to each other are formed. Consequently, it is possible to stably reserve the electric conductive state through the side electrode between the electrode layers, and it is possible to have the piezoelectric element in which the piezoelectric property is stable and excellent and the sensibility deterioration is small. Also, the work for accurately arranging the piezoelectric elements at the desirable arrangement interval can be carried out simply. Moreover, the positional dislocation after the arrangement can be protected. Thus, it is possible to suppress the crosstalk and create the excellent ultrasonic beam.

Also, the ultrasonic transducer according to the present invention is designed such that the plurality of piezoelectric elements, each being the stacked body in which the predetermined numbers of the piezoelectric layers and the electrode layers are alternately stacked and although this has both the sides that are substantially flat along the stacking direction, the side electrodes to connect the predetermined electrode layers are placed outside both of the sides, respectively, are arranged in the direction orthogonal to the stacking direction, wherein since the interval holding layer is formed on the side electrode of at least one piezoelectric element in the piezoelectric elements adjacent to each other, it is possible to stably reserve the electric conductive state through the side electrode between the electrode layers, and it is possible to have the piezoelectric element in which the piezoelectric property is stable and excellent and the sensibility deterioration is small. Also, the work for accurately arranging the piezoelectric elements at the desirable arrangement interval can be carried out simply. Moreover, the positional dislocation after the arrangement can be protected. Thus, it is possible to suppress the crosstalk and create the excellent ultrasonic beam.

Also, the ultrasonic diagnosis apparatus according to the present invention, since using the above-mentioned ultrasonic transducer, can carry out the more accurate diagnosis.

Moreover, the ultrasonic flaw inspection apparatus according to the present invention, since using the above-mentioned ultrasonic transducer, can carry out the more accurate non-destructive inspection.

BEST MODE FOR CARRYING OUT THE INVENTION

The ultrasonic transducer according to the embodiment of the present invention will be described below by using the drawings.

First Embodiment

Figure 1:
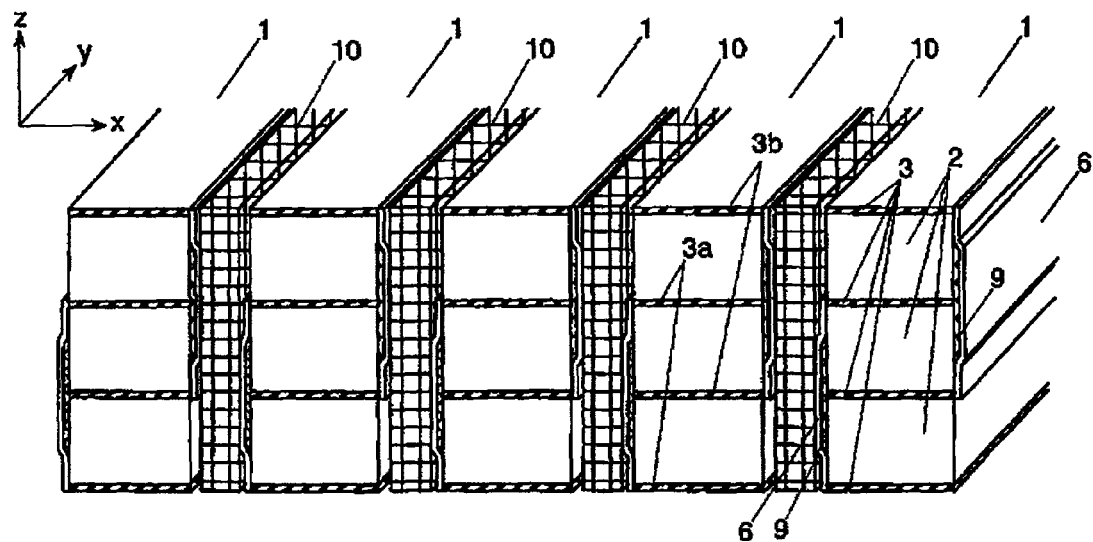
FIG. 1 is a schematic view of a piezoelectric element arrangement configuring an ultrasonic transducer according to a first embodiment of the present invention.

FIG. 1 shows the schematic view of the piezoelectric element arrangement configuring the ultrasonic transducer according to the first embodiment of the present invention. FIG. 1 shows a case in which the five piezoelectric elements 1 are arranged in line in an x-direction that is a direction orthogonal to a stacking direction. However, its number may be arbitrary when it is 2 or more.

The piezoelectric element 1 is configured as the stacked body in which the piezoelectric layer 2 of the three layers and the electrode layer 3 of the four layers are alternately stacked. In FIG. 1, in the electrode layer 3 of the four layers, the upper first layer and third layer serve as the ground electrode layers 3b, and the second layer and the fourth layer of the lowest layer serve as the signal electrode layers 3a. The elongated reed-shaped piezoelectric element in which the piezoelectric layer 2 of the three layers and the electrode layer 3 of the four layers are stacked is formed in advance. Then, on the two substantially flat sides that are wide along the longitudinal direction (y-direction in FIG. 1), for example, when the ground electrode layers 3b of the first layer and the third layer are electrically connected, the insulating layer 9 of the predetermined width is formed on the end surface of the electrode layer 3 which corresponds to the end surface of the signal electrode layer 3a of the second layer and to which an electrical connection is not desired, and the side electrode 6 is formed thereon, and the ground electrode layers 3b of the two layers or the signal electrode layers 3a of the two layers are electrically connected.

The insulating layer 9 is formed, for example, by screen-printing the organic-based material of an epoxy group or a polyimide group, or by coating it by using a dispensing apparatus and the like, or by using an inorganic insulating material such as alumina and the like by using a vacuum thin film deposition method such as sputtering and the like.

The side electrode 6 can be made of metallic materials, for example, gold and the like by similarly using the sputtering and the like. In this way, the side electrodes 6 are formed on the two substantially flat sides that are wide along the longitudinal direction of the piezoelectric element 1 (the y-direction in FIG. 1), and the ground electrode layers 3b of the two layers or the signal electrode layers 3a of the two layers are electrically connected. Consequently, as compared with the case of forming the side electrodes 6 on the two sides (the surfaces along the x-direction in FIG. 1) in which the widths except them are narrow, the width of the side electrode 6 that contributes to the electric connection between the two electrode layers 3 becomes wide. Thus, unless damage and strip occur over the entire width of the side electrode 6 and when the damage and the strip are partial, the conductivity between the two electrode layers 3 can be sufficiently reserved, thereby exhibiting the piezoelectric element 1 in which the piezoelectric characteristic is stable and excellent and the sensitivity deterioration is small.

However, in the case that the piezoelectric elements 1 of stacking structure in which these side electrodes 6 are formed are used to configure the ultrasonic transducer of the array type, this case is configured such that the side electrodes 6 exist on the sides vertical to the arrangement direction of the piezoelectric elements 1. Thus, for example, when the dicing saw and the like are used to divide one plate-shaped stacked body and then form the piezoelectric element arrangement, the insulating layer 9 and the side electrode 6 must be formed on the side that is formed as the result of the formation of the groove for the division. Thus, this case is difficult from the viewpoint of the engineering and working aspects.

So, a method is considered which preliminarily arranges the elongated reed-shaped piezoelectric elements 1, in which the insulating layers 9 and the side electrodes 6 are formed, in line at a desirable arrangement interval and then forms the ultrasonic transducer of the array type.

In FIG. 1, an interval holding member 10 having a thickness that is determined to form a constant interval is arranged between the piezoelectric element 1 and the piezoelectric element 1. At the time of the work for arranging the piezoelectric elements 1, the piezoelectric elements and the interval holding members 10 are alternately arranged, or a structure in which the interval holding member 10 is arranged in advance on the side of the piezoelectric element 1 is formed. Then, the formed structures are arranged, thereby enabling the piezoelectric elements to be arranged in line while always holding the interval defined by the thickness of the interval holding member 10.

Figure 2:
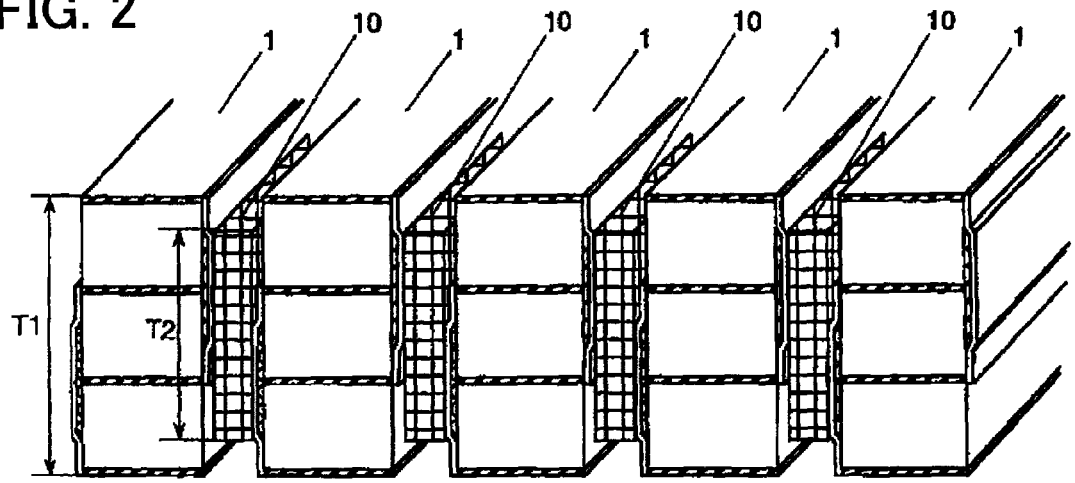
FIG. 2 is a schematic view of another piezoelectric element arrangement configuring the ultrasonic transducer according to the first embodiment of the present invention.

At this time, preferably, as shown in FIG. 2 (the schematic view of another piezoelectric element arrangement configuring the ultrasonic transducer according to the first embodiment of the present invention), a height T2 of the interval holding member 10 is setting to be lower than a height T1 of the piezoelectric element 1 so that the interval holding member 10 does not protrude from the top and bottom portions of the piezoelectric element 1.

Due to such configuration, when, for example, an acoustic matching layer or a rear member is arranged on the top and bottom portions of the piezoelectric element, without any interference of the interval holding member 10, the surface contacts with the top and bottom surfaces of the piezoelectric element are made surer, thereby enabling the excellent property in which the sensibility is high and the frequency band property is wide. The interval holding member 10 is required to have the insulating property so that the adjacent side electrodes 6 are not electrically short-circuited. Also, the thin uniform thickness of about several 10 µm is required. Thus, for example, the film material such as a polyester film or polyimide film is desirable.

Further preferably, a configuration in which, for example, the film material such as the polyester film is used as the base material and for example, acrylic adhesives are placed on both sides of the base material, for example, a double-coated adhesive tape composed of only acrylic adhesive without any base material is suitable. Since the double-coated adhesive tape is used, even if another means such as the adhesive fixing at the time of arranging or after arranging or the keeping of the mechanically locked state in which force continues to be added in the arrangement direction from both ends of the arranged piezoelectric element, once the double-faced tape serving as the interval holding member 10 is arranged between the piezoelectric elements 1, the arrangement state of the piezoelectric elements 1 can be held by the adhesive property of both surfaces. Thus, the arrangement of the piezoelectric elements 1 can be formed at a high precision and the working property is excellent at the same time.

Figure 3:
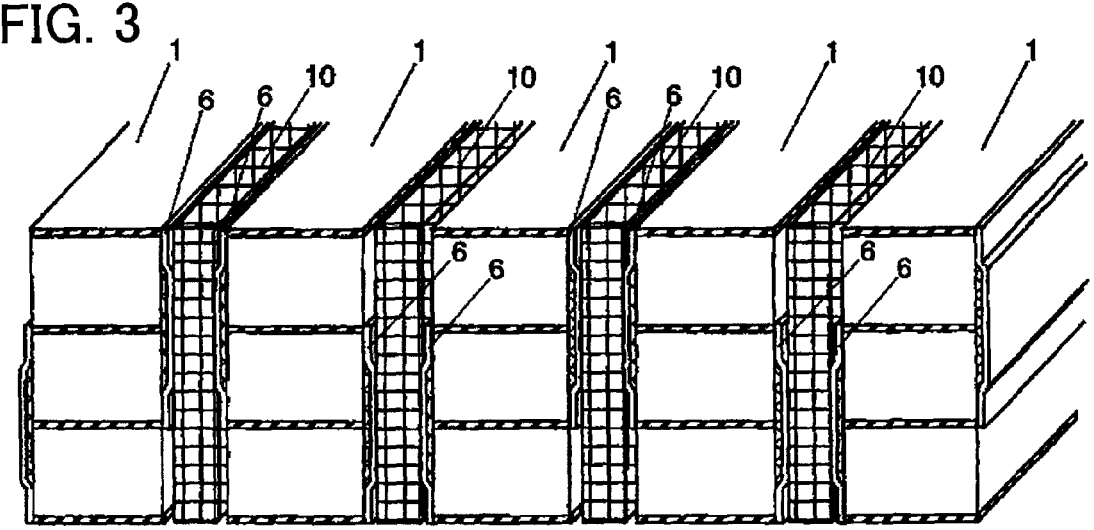
FIG. 3 is a schematic view of still another piezoelectric element arrangement configuring the ultrasonic transducer according to the first embodiment of the present invention.

Also, FIG. 3 shows another schematic view of the piezoelectric element arrangement configuring the ultrasonic transducer according to the first embodiment of the present invention. The difference from FIG. 1 lies in the positional relation between the side electrodes 6 on the sides of the adjacent piezoelectric elements 1.

In FIG. 1, the arrangement is designed in a situation that in all of the piezoelectric elements 1, the side electrodes 6 are arranged at the lower left and upper right positions when viewed from an observer. In FIG. 3, the side electrodes 6 in the piezoelectric element 1 are arranged such that their positions are different every other side electrode 6. In the leftmost piezoelectric element 1, the side electrodes 6 exist at the lower left and upper right positions when viewed from the observer, and in the second leftmost piezoelectric element 1, the side electrodes 6 exist at the upper left and lower right positions when viewed from the observer.

With this arrangement, the side electrodes 6 of the adjacent piezoelectric elements 1 are opposite to each other with the interval holding member 10 between. When viewed from the center of the interval holding member 10, they are bilaterally symmetric, and since the interval holding member 10 is sandwiched between the side electrodes 6 opposite to each other, this arrangement is advantageous in keeping the dimensional precision of the interval.

Figure 4:
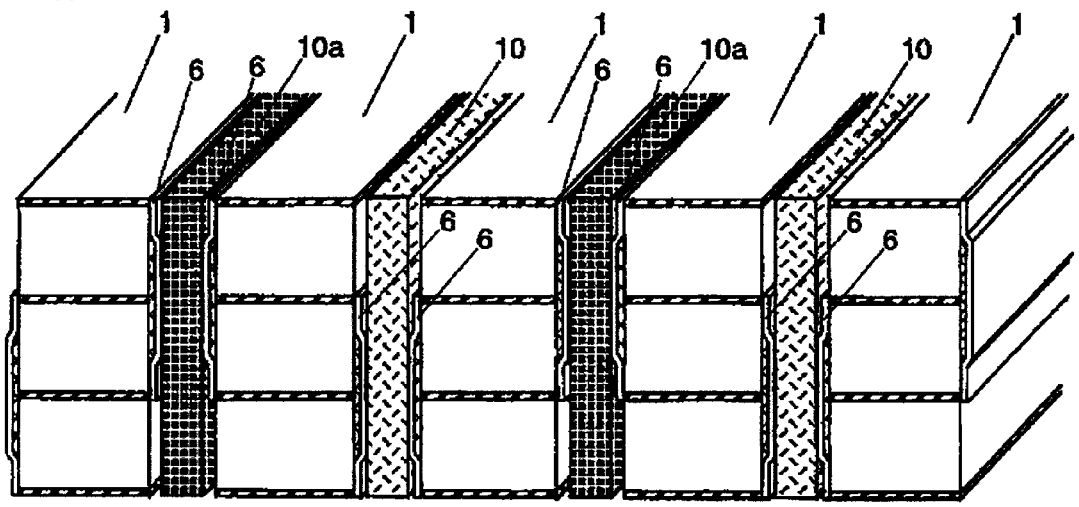
FIG. 4 is a schematic view of still another piezoelectric element arrangement configuring the ultrasonic transducer according to the first embodiment of the present invention.

By the way, in FIG. 3, as for the side electrodes 6 opposite to each other with the interval holding member 10 between, both of them are connected to the ground electrode. Or, they are the electrically common side electrodes 6 that are connected to the signal electrode. So, as shown in FIG. 4 (the schematic view of still another piezoelectric element arrangement configuring the ultrasonic transducer according to the first embodiment of the present invention), an interval holding member 10a existing between the side electrodes 6 connected to the ground electrode is defined as the electric conductive material. Thus, the strong ground connection can be reserved, which improves S/N and contributes to the performance improvement of the ultrasonic transducer.

Also, in the case of the ultrasonic transducer that is used to drive the two piezoelectric elements 1 adjacent to each other at the same time, when all of the interval holding members 10 are made of the electric conductive materials, the two roles of the interval keeping and the electrode connection can be given to the interval holding member 10, and the sure connection of the signal electrode and ground electrode between the two piezoelectric elements 1 can be attained without any different means.

Figure 5:
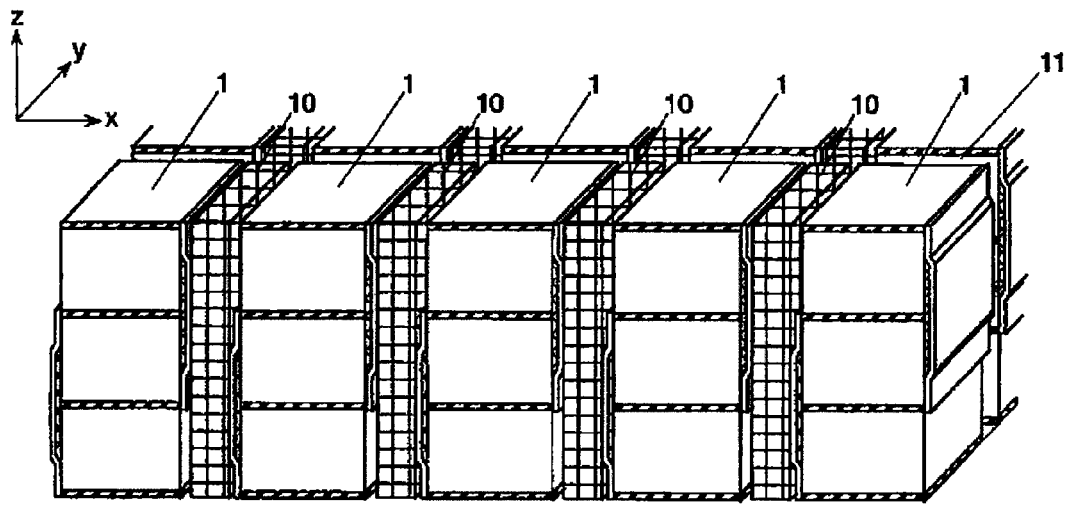
FIG. 5 is a schematic view of a two-dimensional arrangement of piezoelectric elements configuring the ultrasonic transducer according to the first embodiment of the present invention.

By the way, in the explanations from FIG. 1 to FIG. 4, the case of the ultrasonic transducer in which the piezoelectric elements 1 are one-dimensionally arranged is described. However, as shown in FIG. 5, as for the one-dimensionally arranged piezoelectric elements 1, a division groove 11 extending in the x-direction vertical to the arrangement direction is formed, and the piezoelectric elements 1 are divided, thereby enabling the formation of the two-dimensional arrangement. There is a case that the division groove 11 is filled with, for example, epoxy resin and the like. In this way, even the ultrasonic transducer, which has the two-dimensional arrangement of the piezoelectric elements 1 formed by the division after the one-dimensional arrangement of the piezoelectric elements 1, does not depart from the present invention.

Second Embodiment

Figure 6:
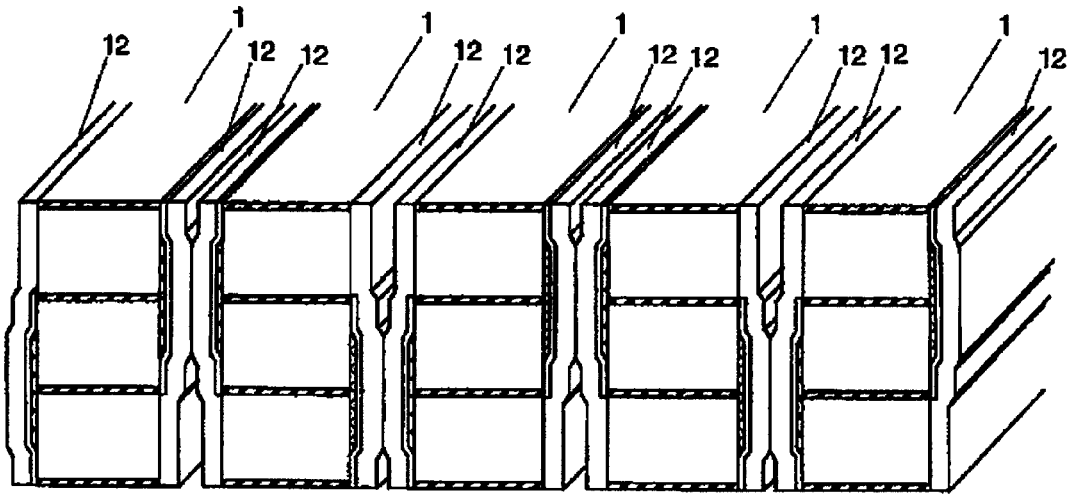
FIG. 6 is a schematic view of a piezoelectric element arrangement configuring an ultrasonic transducer according to the second embodiment of the present invention.

FIG. 6 shows the schematic view of the piezoelectric element arrangement configuring the ultrasonic transducer according to the second embodiment of the present invention. The configuration of the piezoelectric element in which the insulating layer and the side electrode are arranged on the substantially flat side is similar to the first embodiment. Thus, its description is omitted.

In FIG. 6, on the side on which the insulating layer and the side electrode are arranged, the organic insulating material, for example, polyimide, epoxy and the like, is screen-printed or coated, or as for the inorganic insulating material such as alumina and the like, the vacuum thin film deposition method such as sputtering and the like is used to form the interval holding layer having a uniform thickness. The piezoelectric elements on which the interval holding layer are formed are arranged in their original states. Thus, the piezoelectric elements 1 can be accurately arranged at the desirable interval that is determined by the thickness of the interval holding layer. Also, the interval holding layer, since also having a function for protecting the coatings of the insulating layer and the side electrode, has the configuration that is more advantageous for reserving the electric conductive state between the electrode layers through the side electrode.

Figure 7:
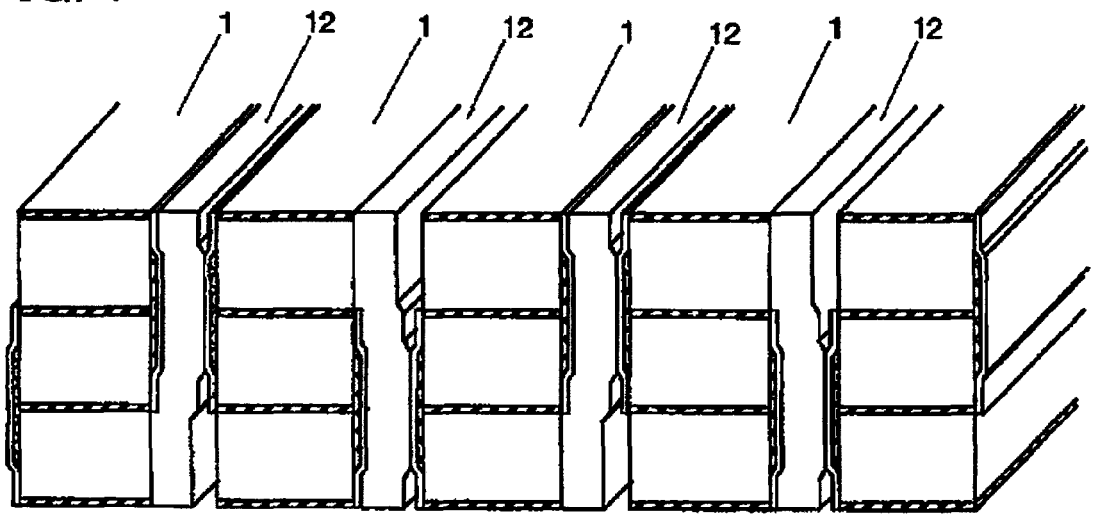
FIG. 7 is a schematic view of another piezoelectric element arrangement configuring the ultrasonic transducer according to the second embodiment of the present invention.

By the way, FIG. 6 is described for the case that the interval holding layers are formed on both of the two sides on which the side electrodes of the piezoelectric element are formed. This is advantageous in view of the effect that the coatings of the side electrodes 6 on the two sides are both protected. However, as shown in FIG. 7, even if the interval holding layer is formed only on one side, this is adequate to hold the arrangement interval. Thus, this configuration is allowable.

Figure 8:
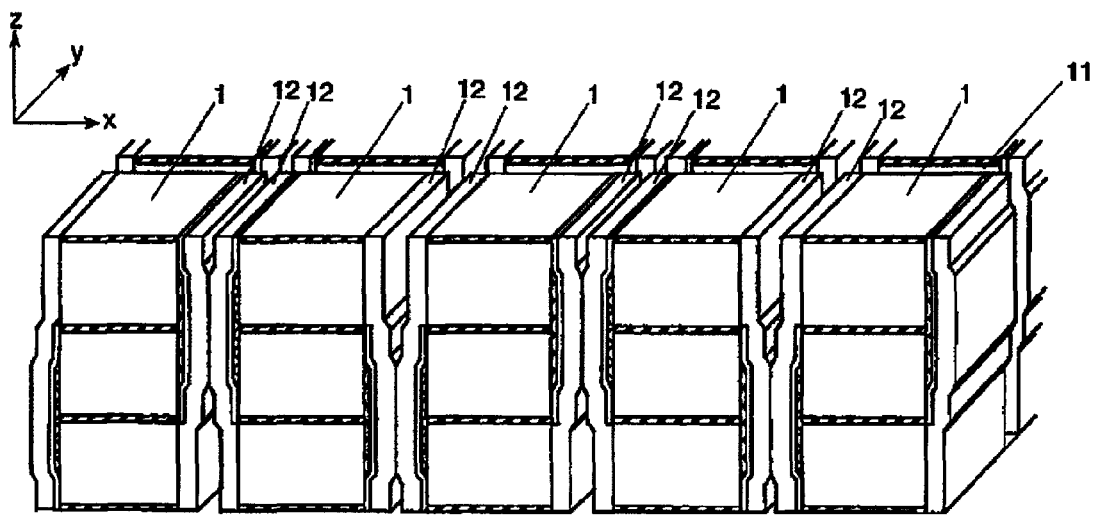
FIG. 8 is a schematic view showing a two-dimensional arrangement of the piezoelectric elements configuring the ultrasonic transducer according to the second embodiment of the present invention.

Also, similarly to the ultrasonic transducer according to the first embodiment, as shown in FIG. 8, even the ultrasonic transducer having the two-dimensional arrangement, in which the one-dimensional arrangement of the piezoelectric elements 1 is divided by the division groove 11, immutably has the effect of the present invention and does not depart from the present invention.

Figure 9:
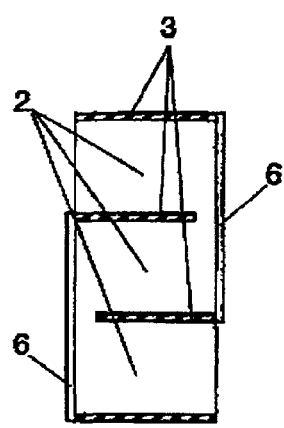
FIG. 9 is a section view of another piezoelectric element configuring the ultrasonic transducer according to the first and second embodiments of the present invention.

By the way, the piezoelectric element 1 described in the first embodiment and the second embodiment is described for the configuration in which the insulating layer 9 is formed on the end surface of the electrode layer 3 to which the electrical connection is not desired and further the side electrode 6 is formed thereon. However, as shown in FIG. 9, in such a way that the end surface of the electrode layer 3 to which the connection is not desired is not exposed onto the side of the piezoelectric element 1, the electrode layer 3 is formed in advance, thereby enabling the formation of the side electrode 6 without any formation of the insulating layer 9. Thus, even the use of the piezoelectric element 1 having this configuration does not depart from the present invention.

Moreover, the first embodiment and the second embodiment are described for the case of the piezoelectric element 1 of stacking structure that is composed of the three piezoelectric layers 2 and the four electrode layers 3. However, the numbers of the piezoelectric layers 2 and the electrode layers 3 are not limited, and their numbers may be arbitrary.

Also, as for the length of the y-direction of the interval holding member 10, which are described in the first embodiment and the second embodiment, and the number required in the y-direction when the piezoelectric elements 1 are divided, the piezoelectric element 1 and the piezoelectric element 1 that are adjacent in the x-direction can be reserved at the constant interval. For example, a configuration is allowable in which the two interval holding members 10 whose lengths are short are arranged at both end portions in the y-direction of one piezoelectric element 1, and the constant interval is reserved at both the end portions of the piezoelectric element 1, or even a configuration in which the short interval holding members 10 are arranged at both ends in the y-direction of the piezoelectric element 1 and the center thereof, and the constant interval is reserved at the three portions does not depart from the present invention.

Third Embodiment

Figure 10:
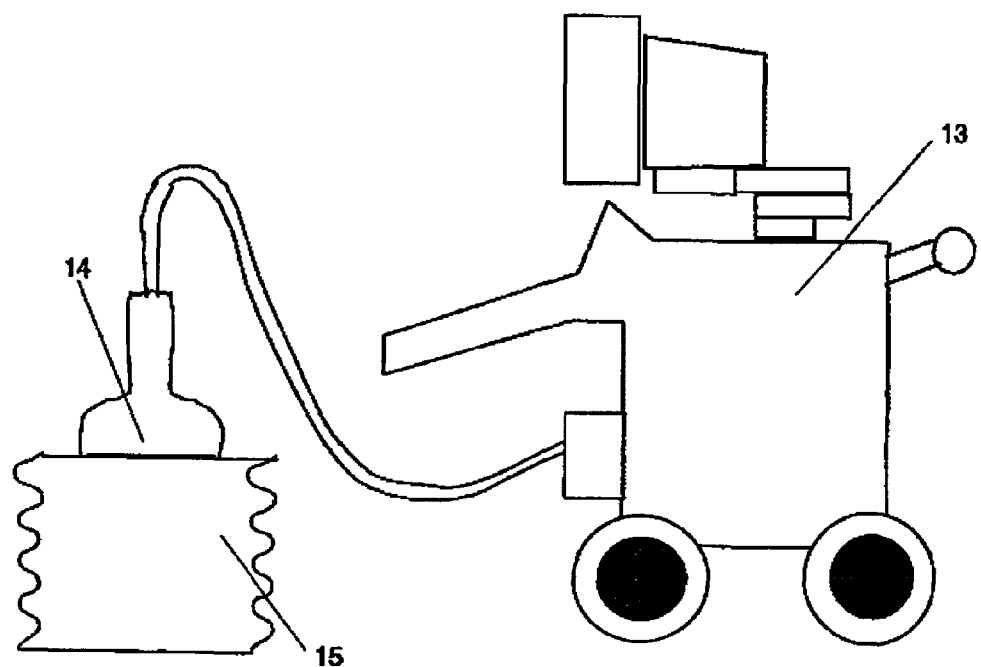
FIG. 10 is a schematic view showing an example of an ultrasonic diagnosis apparatus according to a third embodiment of the present invention.

Next, FIG. 10 shows the schematic view showing one example of the ultrasonic diagnosis apparatus according to the present invention.

The ultrasonic diagnosis apparatus shown in FIG. 10 contains an ultrasonic diagnosis apparatus body 13 and an ultrasonic transducer 14 that is electrically connected thereto. The ultrasonic transducer 14 contains the configuration of the ultrasonic transducer according to the first embodiment and the second embodiment.

The operation of the ultrasonic diagnosis apparatus of the foregoing configuration will be described below. At first, an operator brings the ultrasonic transmission reception surface of the ultrasonic transducer 14 into contact with the body surface of an examinee 15. In this state, an electrical signal (drive signal) is transmitted from the ultrasonic diagnosis apparatus body 13 to the ultrasonic transducer 14.

The drive signal is converted into an ultrasonic wave in the piezoelectric elements inside the ultrasonic transducer 14 and transmitted to the examinee 15. This ultrasonic wave is reflected inside the body of the examinee 15, and a part of a reflection wave is received in the piezoelectric elements inside the ultrasonic transducer 14 and converted into an electrical wave (received signal) and inputted to the ultrasonic diagnosis apparatus body 14. The input received signal is signally processed by the ultrasonic diagnosis apparatus body 13 and outputted as, for example, a diagnostic image to a display such as CRT and the like.

In the foregoing ultrasonic diagnosis apparatus, as the ultrasonic transducer 14, the ultrasonic transducer of the present invention is used which is described in the first embodiment and the second embodiment. According to the foregoing ultrasonic diagnosis apparatus, the merits of the ultrasonic transducer indicated in the first embodiment and the second embodiment can be used to carry out the ultrasonic diagnosis whose precision is high.

Fourth Embodiment

Figure 11:
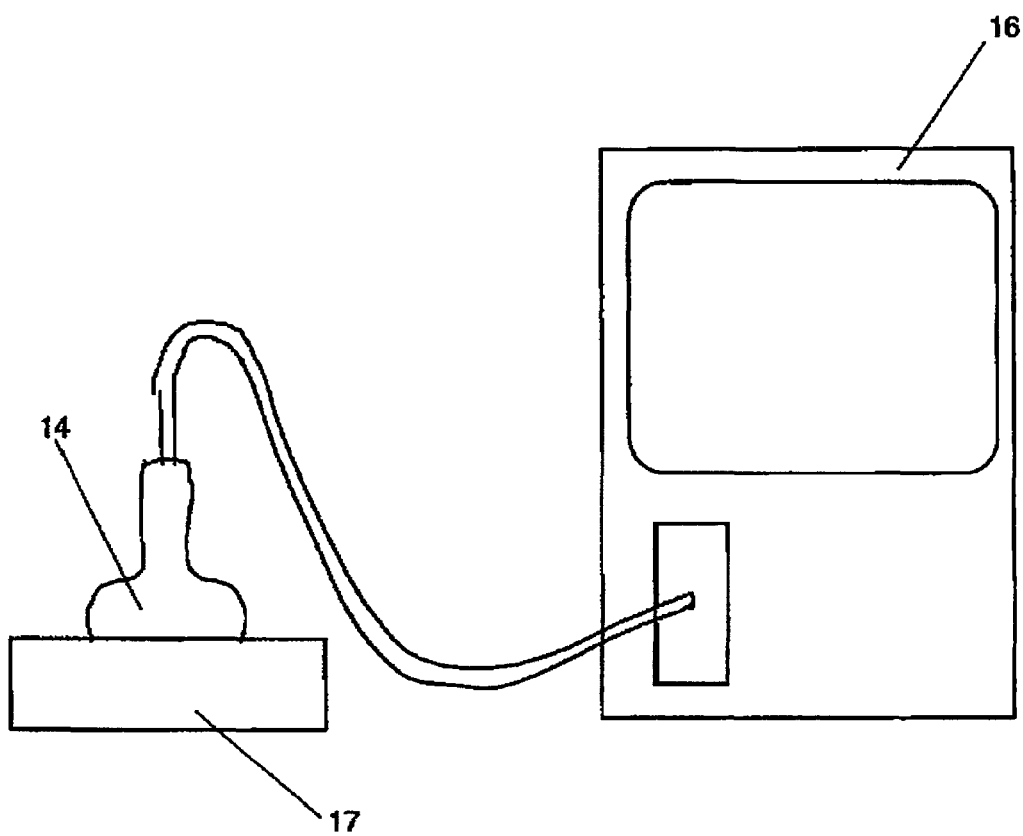
FIG. 11 is a schematic view showing an example of an ultrasonic flaw inspection apparatus according to a fourth embodiment of the present invention.
Figure 12A:
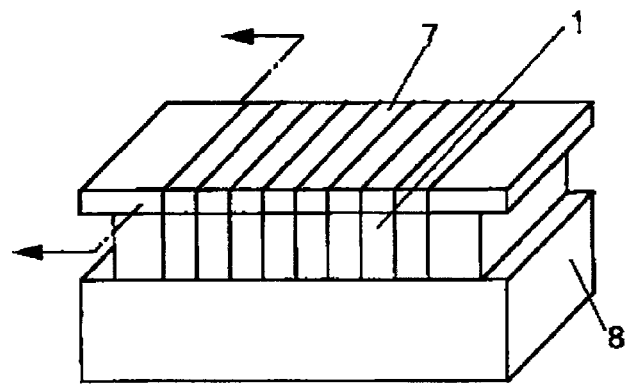
FIG. 12A is a perspective view of a conventionally-known ultrasonic transducer.
Figure 12B:
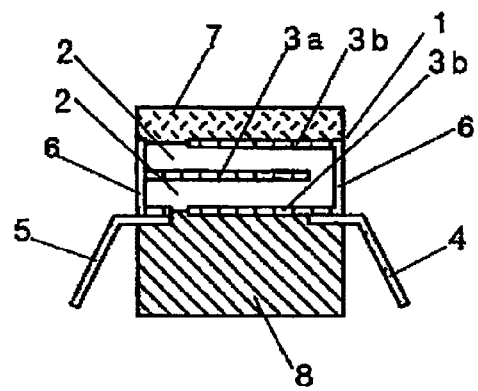
FIG. 12B is a sectional view of the conventionally-known ultrasonic transducer.
Figure 13A:
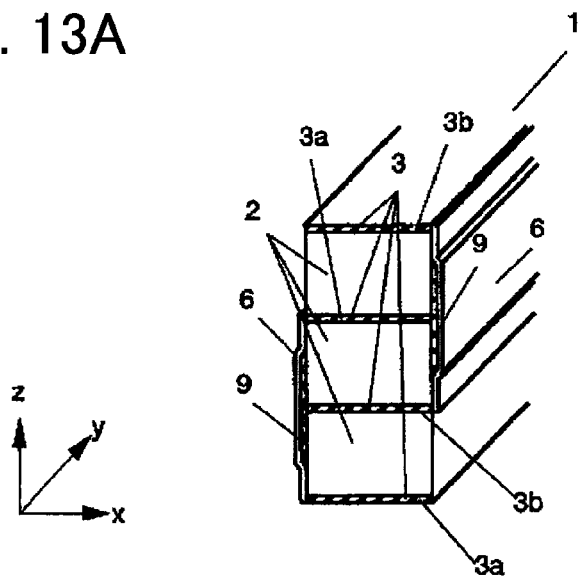
FIG. 13A is a schematic view of a piezoelectric element of a conventionally-known two-dimensional arrangement array ultrasonic transducer.
Figure 13B:
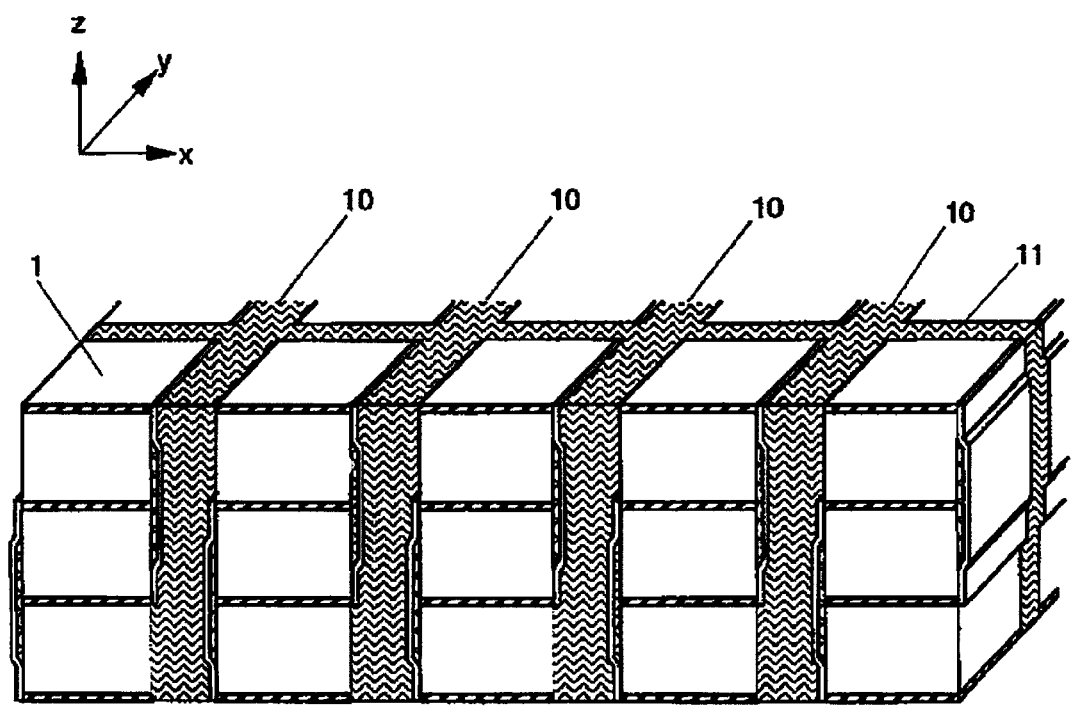
FIG. 13B is a schematic view of the conventionally-known two-dimensional arrangement array ultrasonic transducer.

Next, FIG. 11 shows the schematic view showing one example of the ultrasonic flaw inspection apparatus according to the present invention.

The ultrasonic flaw inspection apparatus shown in FIG. 11 contains an ultrasonic flaw inspection apparatus body 16 and the ultrasonic transducer 14 that is electrically connected thereto. The ultrasonic transducer 14 contains the configuration of the ultrasonic transducer according to the first embodiment and the second embodiment.

The operation of the ultrasonic flaw inspection apparatus of the foregoing configuration will be described below. At first, the operator brings the ultrasonic transmission reception surface of the ultrasonic transducer 14 into contact with the surface of an examinee 17. In this state, an electrical signal (drive signal) is transmitted from the ultrasonic flaw inspection apparatus body 16 to the ultrasonic transducer 14. The drive signal is converted into the ultrasonic wave in the piezoelectric elements inside the ultrasonic transducer 14 and transmitted to the examinee 17.

This ultrasonic wave is reflected by a flaw or a defect inside the examinee 17, and a part of a reflection wave is received in the piezoelectric elements inside the ultrasonic transducer 14 and converted into an electrical wave (received signal) and inputted to the ultrasonic flaw inspection apparatus body 16. The input received signal is signally processed by the ultrasonic flaw inspection apparatus body 16 and displayed as, for example, the inspection image on the CRT and the like.

In the foregoing ultrasonic flaw inspection apparatus, as the ultrasonic transducer 14, the ultrasonic transducer of the present invention is used which is described in the first embodiment and the second embodiment. According to the foregoing ultrasonic flaw inspection apparatus, the merits of the ultrasonic transducer indicated in the first embodiment and the second embodiment can be used to carry out a non-destructive inspection whose precision is high.

This embodiment is described by using the two-dimensional arrangement array. The present invention can be carried out even in the ultrasonic transducer of a different type, independently of the two-dimensional array.

INDUSTRIAL APPLICABILITY

The ultrasonic transducer according to the present invention is designed such that the plurality of piezoelectric elements, each being the stacked body in which the predetermined numbers of the piezoelectric layers and the electrode layers are alternately stacked and although this has both the sides that are substantially flat along the stacking direction, the side electrodes to connect the predetermined electrode layers are placed outside both of the sides, respectively, are arranged in the direction orthogonal to the stacking direction, wherein the interval holding member having the predetermined thickness is put between the sides on which the side electrodes of the piezoelectric elements adjacent to each other are formed. Consequently, it is possible to stably reserve the electric conductive state through the side electrode between the electrode layers, and it is possible to have the piezoelectric element in which the piezoelectric property is stable and excellent and the sensibility deterioration is small. Also, the work for accurately arranging the piezoelectric elements at the desirable arrangement interval can be carried out simply. Moreover, the positional dislocation after the arrangement can be protected. Thus, it is possible to suppress the crosstalk and create the excellent ultrasonic beam.

Moreover, the ultrasonic transducer according to the present invention is designed such that the plurality of piezoelectric elements, each being the stacked body in which the predetermined numbers of the piezoelectric layers and the electrode layers are alternately stacked and although this has both the sides that are substantially flat along the stacking direction, the side electrodes to connect the predetermined electrode layers are placed outside both of the sides, respectively, are arranged in the direction orthogonal to the stacking direction, wherein since the interval holding layer is formed on the side electrode of at least one piezoelectric element in the piezoelectric elements adjacent to each other, it is possible to stably reserve the electric conductive state through the side electrode between the electrode layers, and it is possible to have the piezoelectric element in which the piezoelectric property is stable and excellent and the sensibility deterioration is small. Also, the work for accurately arranging the piezoelectric elements at the desirable arrangement interval can be carried out simply. Moreover, the positional dislocation after the arrangement can be protected. Thus, it is possible to suppress the crosstalk and create the excellent ultrasonic beam.

The ultrasonic diagnosis apparatus that uses this ultrasonic transducer has the effect which enables the accurate ultrasonic diagnosis, and it is effective in the medical field, such as the diagnosis, the treatment and the like. Also, the ultrasonic flaw inspection apparatus that uses this ultrasonic transducer is effective in the industrial field such as the non-destructive inspection and the like.

The inventioned claimed is:

1. An ultrasonic transducer, wherein a plurality of piezoelectric elements, each being a stacked body in which predetermined numbers of piezoelectric layers and electrode layers are alternately stacked and having both sides that are substantially flat along a stacking direction, side electrodes to connect predetermined said electrode layers each other are placed outside both of said sides, respectively, are arranged in a direction orthogonal to said stacking direction, in such a manner that interval holding members each having a predetermined thickness are respectively sandwiched between said sides on which said side electrodes of said piezoelectric elements adjacent to each other are formed wherein each of said interval holding members has a height which is smaller than the height of said sides.

2. The ultrasonic transducer according to claim 1, characterized in that said side electrodes of said piezoelectric elements adjacent to each other are placed on said piezoelectric elements so as to be symmetrical with respect to said interval holding member.

3. The ultrasonic transducer according to claim 2, characterized in that at least one of said interval holding members which are respectively sandwiched between said piezoelectric elements is made of an electric conductive material.

4. The ultrasonic transducer according to claim 1, characterized in that said interval holding member is a double-coated adhesive tape.

5. An ultrasonic transducer, wherein a plurality of piezoelectric elements, each being a stacked body in which predetermined numbers of piezoelectric layers and electrode layers are alternately stacked and although this has both sides that are flat along a stacking direction, side electrodes to connect predetermined said electrode layers each other are placed outside both of said sides, respectively, are arranged in a direction orthogonal to said stacking direction, and wherein an interval holding layer is formed on said side electrode of at least one said piezoelectric element of said piezoelectric elements adjacent to each other before said piezoelectric elements are arranged, said interval holding layer having a height which is smaller than the height of the side of said piezoelectric element.

6. An ultrasonic diagnosis apparatus that includes: the ultrasonic transducer according to claim 1; and an ultrasonic diagnosis apparatus body electrically connected to said ultrasonic transducer.

7. An ultrasonic flaw inspection apparatus that includes: the ultrasonic transducer according to claim 1; and an ultrasonic flaw inspection apparatus body electrically connected to said ultrasonic transducer.

8. An ultrasonic diagnosis apparatus that includes: the ultrasonic transducer according to claim 5; and an ultrasonic diagnosis apparatus body electrically connected to said ultrasonic transducer.

9. An ultrasonic flaw inspection apparatus that includes: the ultrasonic transducer according to claim 5; and an ultrasonic flaw inspection apparatus body electrically connected to said ultrasonic transducer.

10. The ultrasonic transducer according to claim 1, characterized in that said side electrodes of said adjacent piezoelectric elements are opposite to each other with said interval holding member therebetween.

11. The ultrasonic transducer according to claim 5, characterized in that said side electrodes of said adjacent piezoelectric elements are opposite to each other with said interval holding member therebetween.

12. The ultrasonic transducer according to claim 1, characterized in that said electrode layers include ground electrode layers and signal electrode layers, and at least one of said interval holding members existing between said side electrodes connected to said ground electrode layers is made of an electric conductive material.

13. The ultrasonic transducer according to claim 5, characterized in that said electrode layers include ground electrode layers and signal electrode layers, and at least one of said interval holding members existing between said side electrodes connected to said ground electrode layers is made of an electric conductive material.

* * * * *